(12) United States Patent
Kasai et al.

(10) Patent No.: US 9,028,456 B2
(45) Date of Patent: May 12, 2015

(54) INFUSION PUMP

(75) Inventors: Takashi Kasai, Tokyo (JP); Kenji Honda, Tokyo (JP)

(73) Assignee: Namiki Seimitsu Houseki Kabushiki Kaisha, Tokyo (JP)

( * ) Notice: Subject to any disclaimer, the term of this patent is extended or adjusted under 35 U.S.C. 154(b) by 1949 days.

(21) Appl. No.: 12/112,247

(22) Filed: Apr. 30, 2008

(65) Prior Publication Data

US 2009/0306592 A1 Dec. 10, 2009

(51) Int. Cl.
| | |
|---|---|
| A61M 5/00 | (2006.01) |
| F04B 43/12 | (2006.01) |
| A61M 5/142 | (2006.01) |
| A61M 39/28 | (2006.01) |
| F04B 43/08 | (2006.01) |
| F04B 49/10 | (2006.01) |

(52) U.S. Cl.
CPC ............ F04B 43/12 (2013.01); A61M 5/14228 (2013.01); A61M 39/281 (2013.01); F04B 43/082 (2013.01); F04B 49/10 (2013.01)

(58) Field of Classification Search
USPC .......................... 604/246, 249, 250, 153, 151
See application file for complete search history.

(56) References Cited

U.S. PATENT DOCUMENTS

| | | | |
|---|---|---|---|
| 5,401,256 A | 3/1995 | Stone et al. | |
| 6,629,955 B2 * | 10/2003 | Morris et al. | ................ 604/153 |
| 2007/0270765 A1 | 11/2007 | Hasler | |

FOREIGN PATENT DOCUMENTS

| | | |
|---|---|---|
| JP | 5-277183 | 10/1993 |
| JP | 5-277186 | 10/1993 |
| JP | 2000-237308 A | 9/2000 |

OTHER PUBLICATIONS

International Search Report with mailing date of Jul. 14, 2009; International Application No. PCT/JP2009/001952 with English Translation.

The Written Opinion from International Searching Authority/ Japanese Patent Office with mailing date of Jul. 14, 2009; International Application No. PCT/JP2009/001952.

* cited by examiner

*Primary Examiner* — Aarti B Berdichevsky
*Assistant Examiner* — Laura Schell
(74) *Attorney, Agent, or Firm* — Studebaker & Brackett PC

(57) ABSTRACT

An infusion pump is provided with a slide clamp mechanism having a clamp member for closing or opening an infusion tube and a valve mechanism for pressing the infusion tube to stop flow of a solution in the infusion tube and has a structure where an interlocking mechanism for interlocking the slide clamp mechanism with the valve mechanism only by manipulation of a handle is disposed. During a series of manipulations of the handle, the infusion tube is always closed by one or both of the slide clamp and valves 14A and 14B, so that free flow of a solution in the infusion tube 40 can be entirely prevented.

11 Claims, 9 Drawing Sheets

(a)

(b)

(a)

(b)

(a)

(b)

(c)

INFUSION PUMP

TECHNICAL FIELD

The present invention relates to an infusion pump used for a medical intravenous apparatus or the like, and more particularly, to an infusion pump having a tube closing mechanism for preventing free flow of a fluid in an opened state of a tube for feeding the fluid.

BACKGROUND ART

Conventionally, a peristaltic infusion pump is mainly used as a medical infusion pump for feeding a medicinal solution or the like in an infusion tube, in which a door is openably and closably provided to an infusion pump body having a pump mechanism.

The peristaltic infusion pump has a structure for performing feed, in which a plurality of fingers provided to a pump mechanism body perform reciprocating motion with individual phases to be in a peristaltic movement as a whole, so that infusion tubes disposed between a finger and a receiving plate provided to the door are sequentially pressed toward a downstream so as to perform the feed. An example of the peristaltic infusion pump is disclosed in Japanese Patent Application Publication No. 5-277183.

In such an infusion pump, in a case where the infusion tube is unfitted after the door provided to the infusion pump is opened, if some portion in the infusion pump is not closed by using a klemme or the like prior to the opening of the door, a solution in the infusion tube may be free-flown due to its weight at the same time of opening the door. Therefore, an infusion pump having a function of preventing the free flow is desired.

An example of the infusion pump having a function of preventing the free flow is disclosed in Japanese Patent Application Publication No. 5-277186.

According to a structure of the infusion pump disclosed in Patent Document 2, a mechanism for closing the infusion tube at the same time of opening the door is provided, and if the infusion tube is not closed by a predetermined closing member, the infusion tube cannot be detached. Therefore, the infusion pump has a good safety for preventing the free flow.

SUMMARY OF THE INVENTION

However, according to the structure of the infusion pump disclosed in Japanese Patent Application Publication No. 5-277186, the following problems relating an operator's burden and mistake may occur during the manipulation of fitting or unfitting of the infusion tube to or from the infusion pump.

Firstly, in terms of the operator's burden, many steps of manipulations are required. For example, at the time of fitting the infusion tube, a manipulation of opening a mechanism (hereinafter, referred to as a safety clamp) for closing the infusion tube is required; and at the time of unfitting the infusion tube, a manipulation of closing a clamp member (hereinafter, referred to as a slide clamp) for the infusion tube and a manipulation of opening the safety clamp are required.

In addition, at the manipulation of opening the safety clamp, the operator pushes a portion of the mechanism of the safety clamp with the finger. Since the safety clamp is constructed with a strong spring for surely closing the infusion tube, the manipulation may be a heavy burden on some operators.

If the safety clamp is designed to be automatically or semi-automatically opened by using a driving source such as a motor in order to reduce load and burden on the operator, other problems of "an increase in the number of parts", "an increase in space required for internal structure", "non-drivability under no power" and "high cost" occurs.

Next, in terms of the operator's mistake, at the time of unfitting the infusion tube, the operator may push the safety clamp with the finger before closing the infusion tube with the slide clamp. Therefore, if the operator manipulates in an erroneous sequence, the free flow may occur.

In order to solve the problems, the present invention provides an infusion pump of feeding a solution in an infusion tube, wherein the infusion pump comprises a pump body and a door unit which can be opened and closed with respect to the pump body. The detailed structure thereof is as follows.

The door unit constitutes a door mechanism part, and the door mechanism part comprises a door which is supported with a shaft by the pump body and an engagement portion for the pump body and has a structure having a handle which is supported with a shaft by the door to rotatably move in a predetermined range.

The pump body comprises a feeding mechanism part, a slide clamp mechanism part, a valve mechanism part, and an interlocking mechanism part, and the feeding mechanism part has a structure having a driving part for pressing the infusion tube through a reciprocating motion.

The slide clamp mechanism part has a structure having a clamp holding part for holding the clamp member that allows the infusion tube to be in a closed state or an opened state and a clamp moving part for moving a clamp member.

The valve mechanism part has a structure having a valve capable of blocking a fluid channel of a solution in the infusion tube by pressing the infusion tube.

The interlocking mechanism part has a structure having a plurality of links for transferring a force exerted thereto through a rotating motion of the handle to the slide clamp mechanism part and the valve mechanism part.

The handle is engaged with the pump body, and the clamp member closes or opens the infusion tube due to force exertion when the handle is rotated.

The valve closes the fluid channel of the solution in the infusion tube by pressing the infusion tube or opens the fluid channel of the solution in the infusion tube by releasing the pressing of the infusion tube.

The invention further provides an infusion pump wherein a state that the clamp member closes the infusion tube and the valve does not press the infusion tube is changed into another state by engaging the handle with the pump body and exerting a force through rotation of the handle from the one limit position to the other limit position in a rotatable range on the plurality of links of the interlocking mechanism part.

Next, at least one or more links operate on the valve mechanism part so as for the valve to press the infusion tube, and after that, at least one or more links operate on the slide clamp mechanism part so that the clamp moving part moves the clamp member from a position corresponding to a closed state of the clamp member to a position corresponding to an opened state thereof.

In addition, the state that the clamp member opens the infusion tube and the valve presses the infusion tube is changed into another state by engaging the handle with the pump body and exerting the force through rotation of the handle from the one limit position to the other limit position in the rotatable range on the plurality of links of the interlocking mechanism part.

Next, at least one or more links operate on the slide clamp mechanism part so as for the clamp moving part to move the clamp member from the position corresponding to the opened state of the clamp member to the position corresponding to the closed state thereof, and after that, at least one or more links operate on the valve mechanism part so that the valve releases the pressing of the infusion tube.

The invention further provides an infusion pump wherein the driving part of the feeding mechanism part is provided with an approximately V-shaped groove portion along the feeding direction in the infusion tube.

The door part of the door mechanism part is provided with an opposite part where an approximately V-shaped groove portion is formed at an opposite position of the driving part in a state that the door unit is closed, and at least one valve of the valve mechanism is disposed at a position that the infusion tube can be closed at both sides of the driving part.

The driving part performs reciprocating motion in a direction perpendicular to the feeding direction and in a direction parallel to the opposite door unit, so that the driving part and the opposite part repetitively press the infusion tube, and the valve is operated in synchronization with a timing that the infusion tube is repetitively pressed, so that the solution in the infusion tube is fed.

Still further, the invention provides an infusion pump wherein the driving part of the feeding mechanism part is constructed with a plurality of finger parts.

Each of the finger parts performs reciprocating motion, so that distal ends of the finger parts sequentially and repetitively press the infusion tube in the feeding direction to feed the solution in the infusion tube in a peristaltic manner.

Also the invention provides an infusion pump, wherein the interlocking mechanism part for interlocking and operating the slide clamp mechanism part and the valve mechanism part only through manipulation of the handle has a link mechanism part having a plurality of degrees of freedom and a three-axis direction movable range.

In addition, springs for forcing the interlocking mechanism part are disposed to at least one or more positions of the pump body.

The invention further provides an infusion pump, wherein the interlocking mechanism part for interlocking and operating the slide clamp mechanism part and the valve mechanism part only through manipulation of the handle has a structure where a plurality of links including a link having a groove cam or a slider portion are provided in combination.

In addition, springs for forcing the interlocking mechanism part are disposed to at least one or more positions of the pump body.

According to the invention in a state that the door unit is opened with respect to the pump body, since an operator does not need to manually open and close the valve corresponding to a conventional safety clamp, free flow caused from mistake in manipulation cannot occur.

In addition, the operator can operate a mechanism for closing and opening the infusion tube with a relatively small force by using a link mechanism having a lever function without use of a driving power source such as a motor for which electric power is required.

In addition, since a series of operations where the slide clamp mechanism and the valve mechanism are operated in interlock with each other can be performed only through the manipulation of the handle, the operator cannot manipulate in an erroneous sequence.

Since the infusion tube is always closed by the clamp member, the valve, or both of the clamp member and the valve at the time of fitting or unfitting the infusion tube to or from the infusion pump, the free flow can be surely prevented.

After completion of the manipulation of closing the door unit to fit the infusion tube to the infusion pump, the valve is in the state of closing the infusion tube. However, since the infusion tube is pressed by a single part, that is, the driving part, the valve can be opened to feed a solution at a suitable time by using the simple structure.

Since the peristaltic type is used, the valve does not need to be opened and closed in synchronization with operation timing of the driving part of the feeding mechanism, so that only a single valve may be employed.

Further, since the spring for exerting a force on the interlocking mechanism is provided, parts of the interlocking mechanism may be located at predetermined positions when a force is not exerted on the interlocking mechanism according to some manipulation of the handle.

In addition, if the handle is manipulated in a state that the door unit is completely locked with the pump body, the force of the spring is exerted on the handle through the links, so that operators can easily identify the state that the door unit is not completely locked with the pump body.

The link having a groove cam is used as one of the links constituting the interlocking mechanism, so that the timings when the slide clamp mechanism and the valve mechanism function can be determined by using a single link.

BRIEF DESCRIPTION OF THE DRAWINGS

Hereinafter, infusion pumps according to preferred embodiments of the present invention will be described with reference to the accompanying drawings. In the embodiments, the same elements are denoted by the same reference numerals.

FIG. 1 is a perspective view illustrating an infusion pump 100 according to a first embodiment of the present invention. The infusion pump 100 is mainly constructed with a pump body 10 and a door unit 20 which is openably and closably provided to the pump body 10. In FIG. 1(*a*), the door unit is in an opened state. In FIG. 1(*b*), the door unit is in a closed state.

Figure 1:
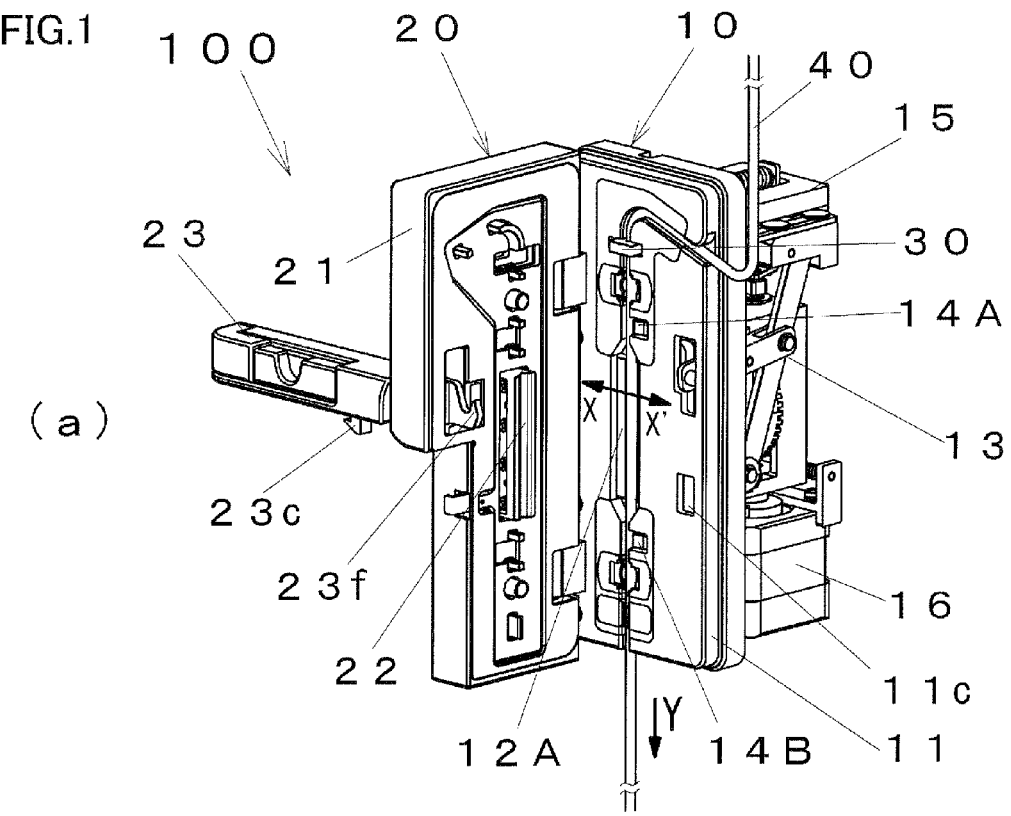
FIGS. 1(*a*) and (*b*) are a perspective views illustrating an infusion pump according to an embodiment of the present invention.
Figure 1:
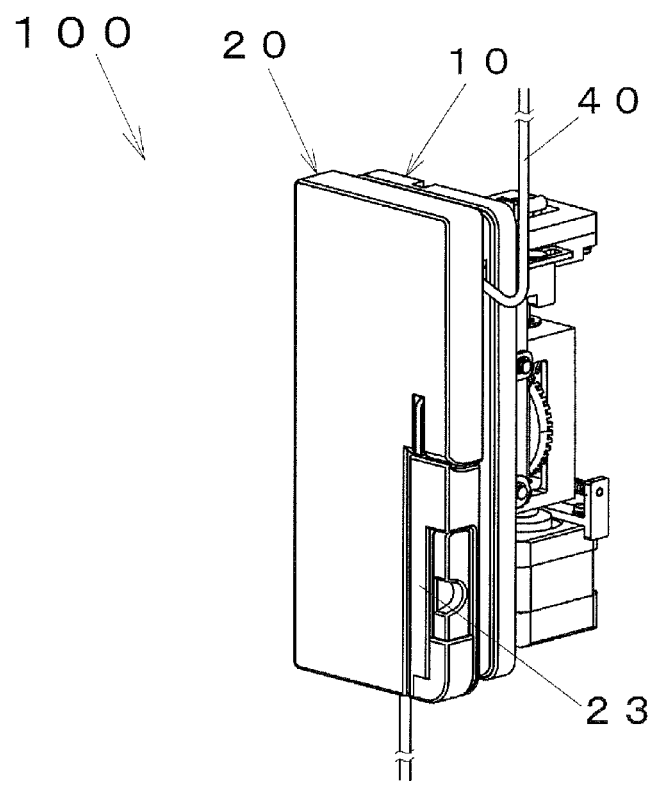

In the embodiment, closing and opening of the infusion tube are performed by a valve mechanism and a slide clamp mechanism which function in interlock with a series of manipulations of a handle 23 in a process where, in the opened state of the door unit shown in FIG. 1(*a*), the infusion tube 40 is fitted in the pump body in a state that the infusion tube is closed by a slide clamp 30, and after that, the door unit is in the closed state shown in FIG. 1(b).

During the opening and closing of the door unit 20 by a series of manipulations of the handle 23, the infusion tube 40 is always closed by one or both of the slide clamp 30 and valves 14A and 14B, so that free flow of a solution in the infusion tube 40 can be entirely prevented.

More specifically, positions of the handle 23 shown in FIGS. 6(a) to (d) correspond to the closing or opening of the infusion tube 40 by the slide clamp 30 and the valves 14A and 14B as the states listed in the following table.

Figure 6:
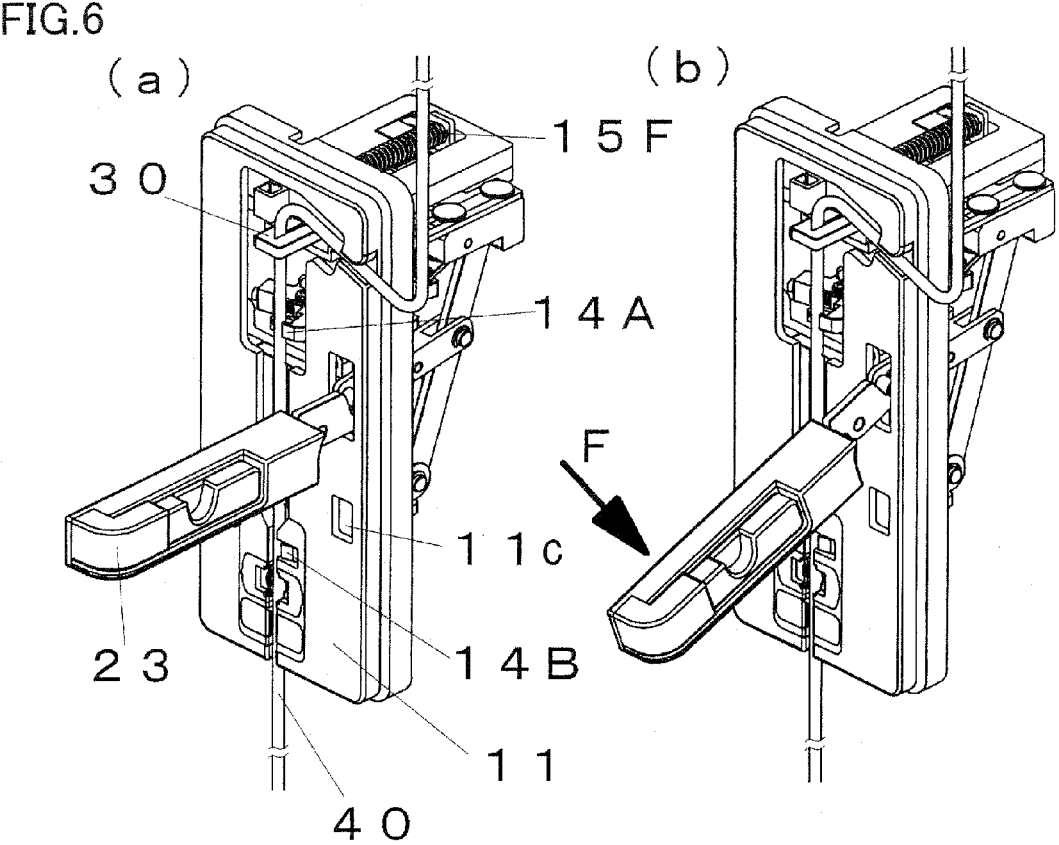
FIGS. 6(*a*), (*b*), and (*c*) are views illustrating a position of a handle and states of a slide clamp and valves according to the embodiment of the present invention.
Figure 6:
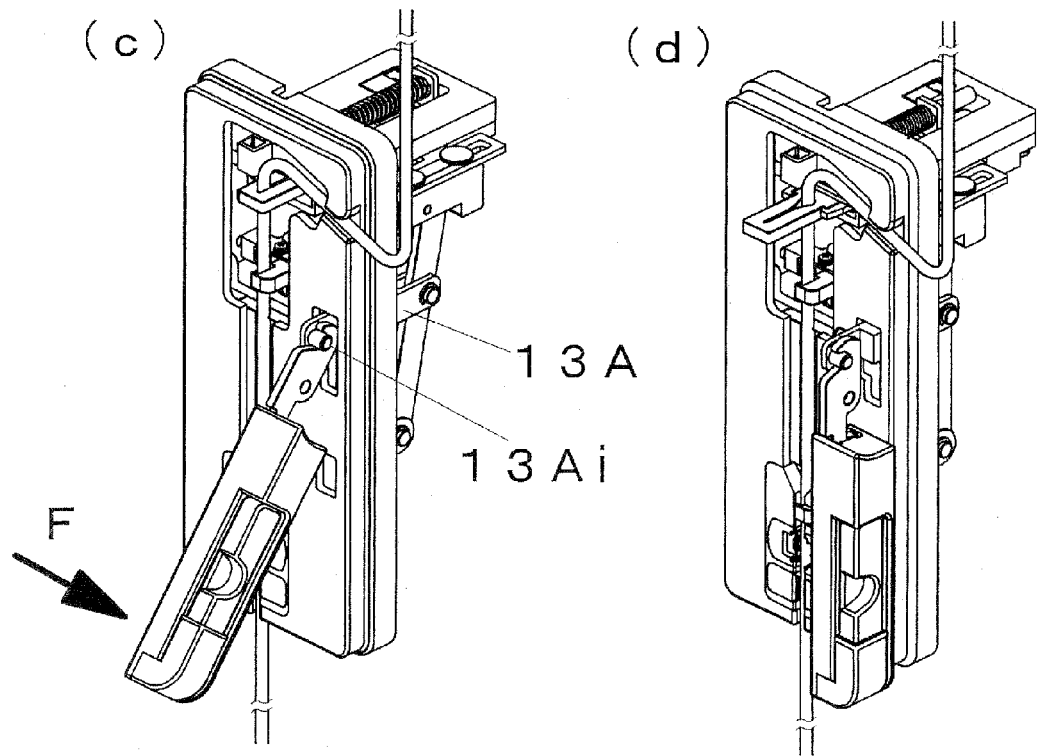

| Position of Handle (FIG. 6) | Slide Clamp 30 | Valves 14A and 14B |
|---|---|---|
| FIG. 6 (a) | Closed | Opened |
| FIG. 6 (b) | Closed | Opened |
| FIG. 6 (c) | Closed | Closed |
| FIG. 6 (d) | Opened | Closed |

Hereinafter, a structure and function of the infusion pump 100 according to the embodiment for obtaining the states listed in the above table will be described in detail.

The pump body 10 is mainly constructed with a valve mechanism part having a valve 14A and a valve 14B, a slide clamp mechanism part 15, an interlocking mechanism part 13, a shuttle mechanism part having a V-grooved driving part 12A, and a motor 16, which are disposed on a base plate 11.

The door unit 20 is mainly constructed with the handle 23 provided to a door part 21 and a V-grooved fixing part 22.

Figure 2:
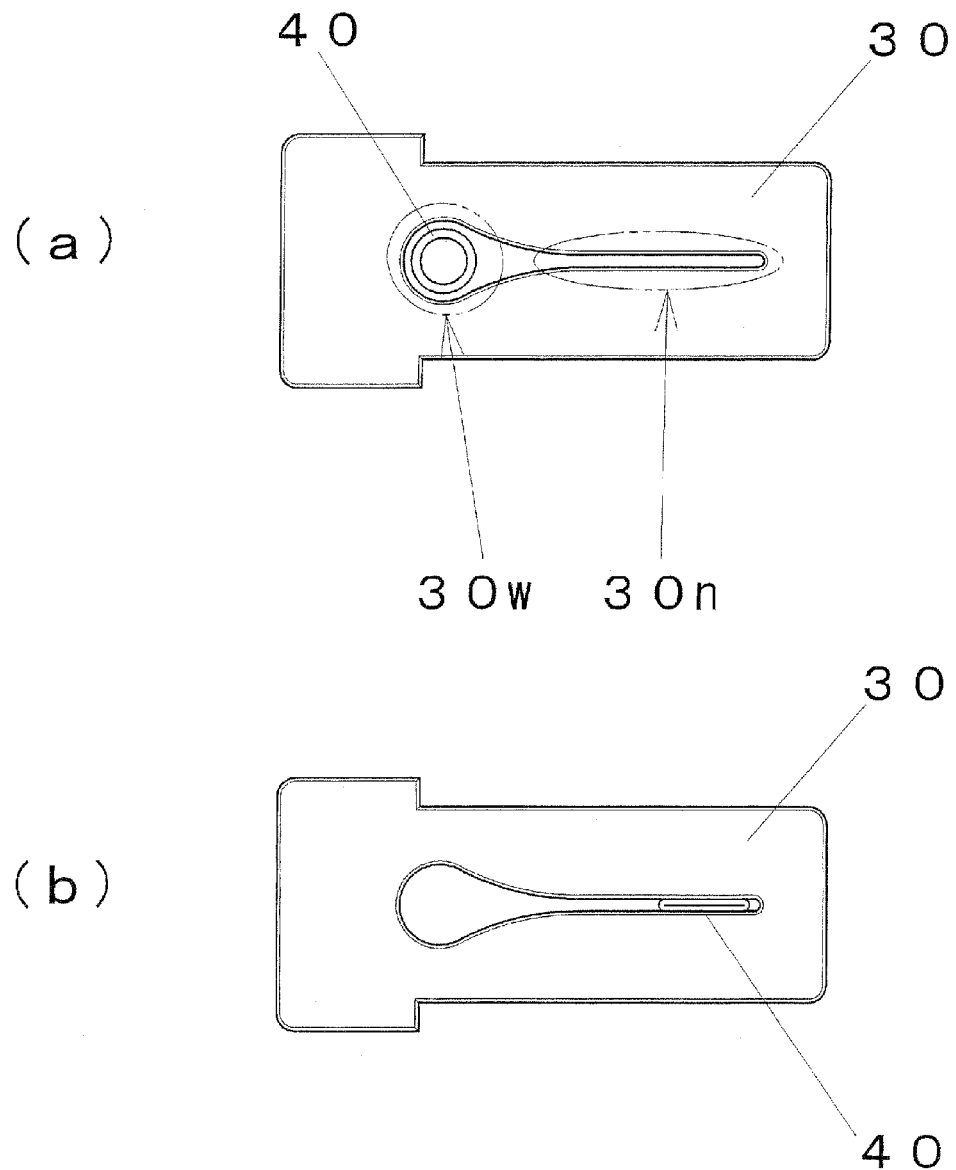
FIGS. 2(*a*) and (*b*) are views illustrating a clamp member of the infusion tube according to the embodiment of the present invention.

FIG. 2(a) is a plan view illustrating the slide clamp 30 used as a clamp member for closing the infusion tube 40. The slide clamp 30 has a penetrating groove of which groove width is varied from a narrow-width groove portion 30n to a wide-width groove portion 30w.

The narrow-width groove portion 30n has a width smaller than twice the wall thickness of the infusion tube 40, and the wide-width groove portion 30w has a width larger than the external diameter of the infusion tube. Therefore, when the infusion tube is positioned at the narrow-width groove portion 30n, the infusion tube 40 is closed as shown in FIG. 2(b); and when the infusion tube is positioned at the wide-width groove portion 30w, the infusion tube 40 is opened as shown in FIG. 2(a).

Hereinafter, structures of mechanisms included in the infusion pump according to the present embodiment, particularly, a feeding mechanism part, a valve mechanism part, a slide clamp mechanism part, and an interlocking mechanism part will be described in detail.

The infusion pump according to the present embodiment uses a shuttle-type feeding mechanism in which a solution in the infusion tube is fed by allowing the V-grooved driving part 12A to perform reciprocating motion in a direction X-X' perpendicular to a feeding direction Y and parallel to the V-grooved fixing part 22 opposite thereto by using a motor 16 as a driving source so that the V-grooved fixing part 22 may repetitively press the infusion tube.

Figure 3:
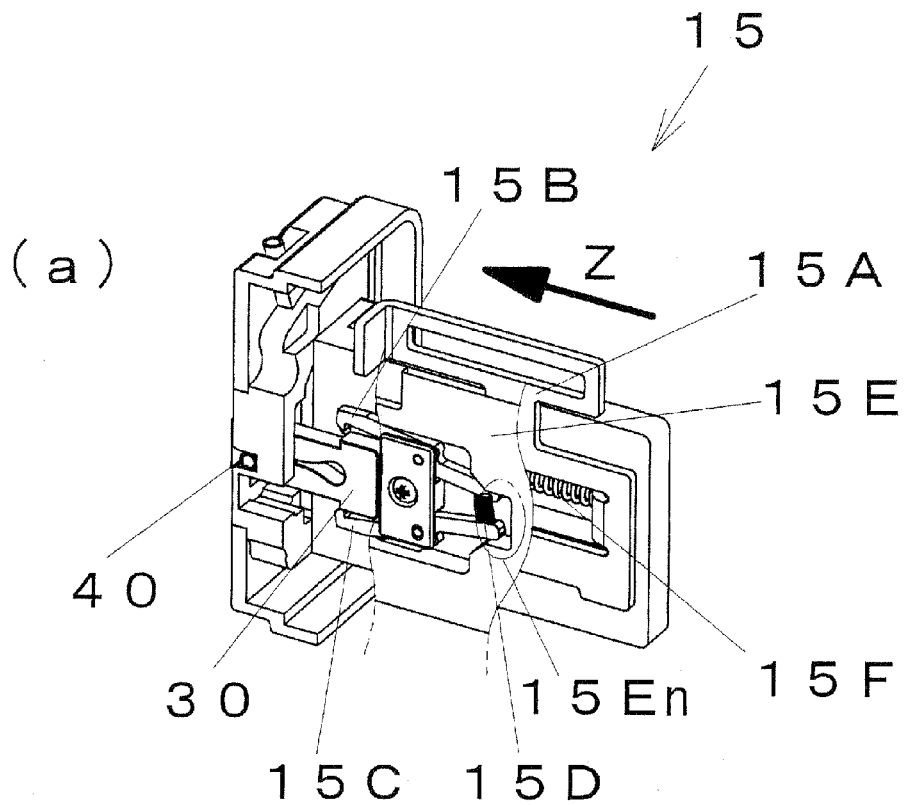
FIGS. 3(*a*) and (*b*) are views illustrating a structure of a slide clamp mechanism according to the embodiment of the present invention.
Figure 3:
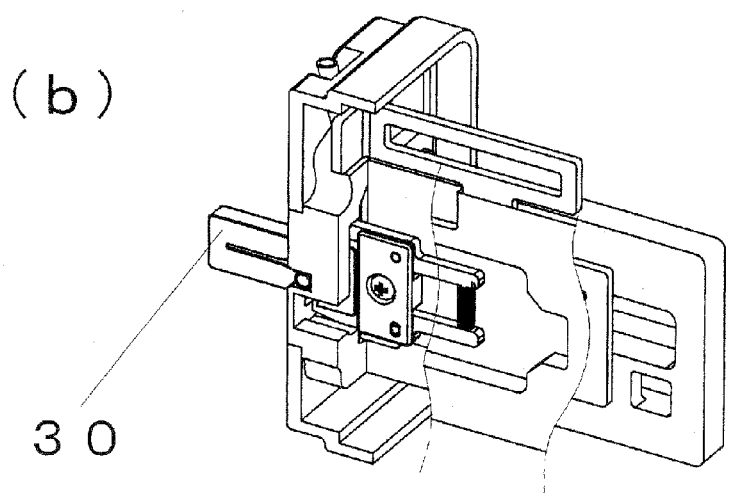

FIG. 3 illustrates a structure of the slide clamp mechanism part 15. The slide clamp mechanism part 15 is mainly constructed with a slide part 15A, arms 15B, and 15C, an arm spring 15D, a slider case 15E, and a slider spring 15F.

FIG. 3(a) illustrates a state that the slide clamp 30 that closes the infusion tube 40 with the narrow-width groove portion 30n is mounted on the slide clamp mechanism part 15.

When the slider spring 15F exerts a force on the slide part 15A and any other external forces are not exerted thereto, the state of FIG. 3(a) is maintained.

In this case, ends of the arms 15B and 15C are positioned at a narrow-width portion 15En of the slider case 15E.

If the slide part 15A is further exerted with a force to be moved toward the slide clamp 30 (in the Z direction of FIG. 3(a)), the state of FIG. 3(a) is changed into a state of FIG. 3(b) in which the infusion tube 40 is positioned at the wide-width groove portion 30w of the slide clamp 30 to be opened.

When the ends of the arms 15B and 15C are separated from the narrow-width portion 15En of the slider case 15E, only the arm spring 15D exerts the force, so that the arms 15B and 15C hold the slide clamp 30.

Figure 4:
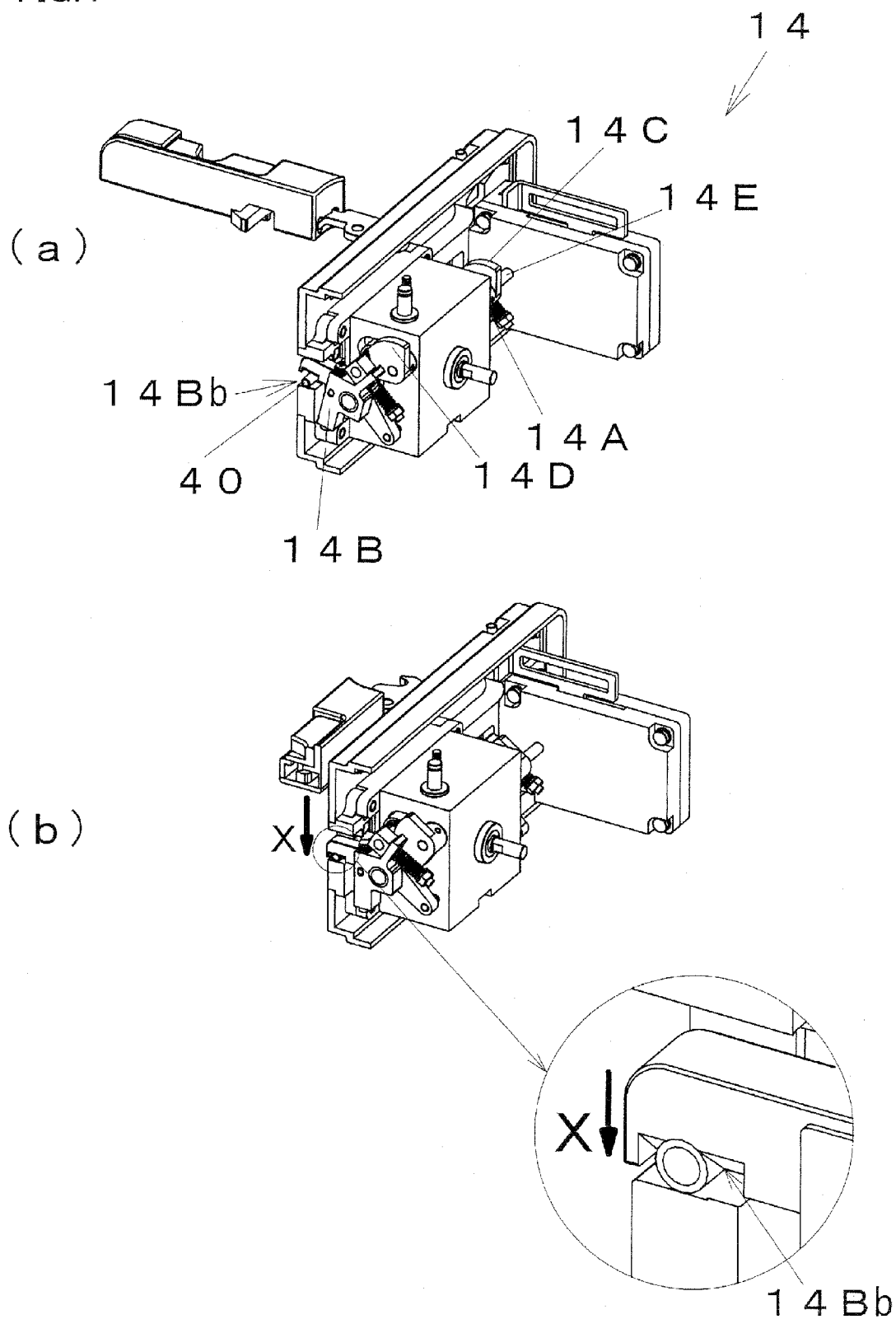
FIGS. 4(*a*) and (*b*) are views illustrating a structure of a valve mechanism according to the embodiment of the present invention.

FIG. 4 illustrates a structure of the valve mechanism part 14. The valve mechanism part 14 is mainly constructed with valves 14A and 14B, valve cams 14C, and 14D, and a valve cam shaft 14E.

FIG. 4(a) illustrates a state that the valves 14A and 14B are opened. Namely, the above state is a state that closing portions 14Ab (see FIG. 7) and 14Bb of the valves 14A and 14B with respect to the infusion tube 40 do not close a fluid channel when the valves 14A and 14B does not press the infusion tube 40 in the X direction of FIG. 4(b).

If the valve cam shaft 14E is rotated in the state of FIG. 4(a), positions of the valve cams 14C and 14D integrally formed with the valve cam shaft 14E are changed into positions for exerting a force on the valves 14A and 14B, so that the closing portions 14Ab and 14Bb for the infusion tube 40 are moved in the X direction.

Accordingly, the valves 14A and 14B presses the infusion tube to close the fluid channel, which is the state that the valves 14A and 14B are closed.

Figure 5:
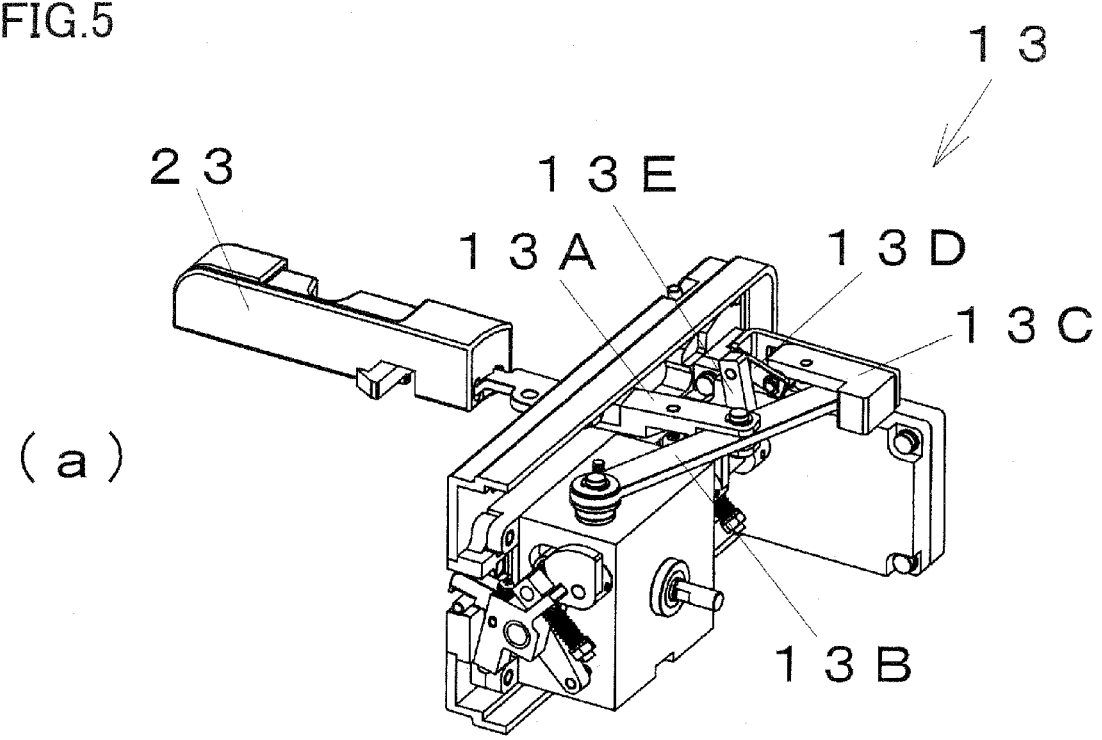
FIGS. 5(*a*) and (*b*) are views illustrating a structure of an interlocking mechanism according to the embodiment of the present invention.
Figure 5:
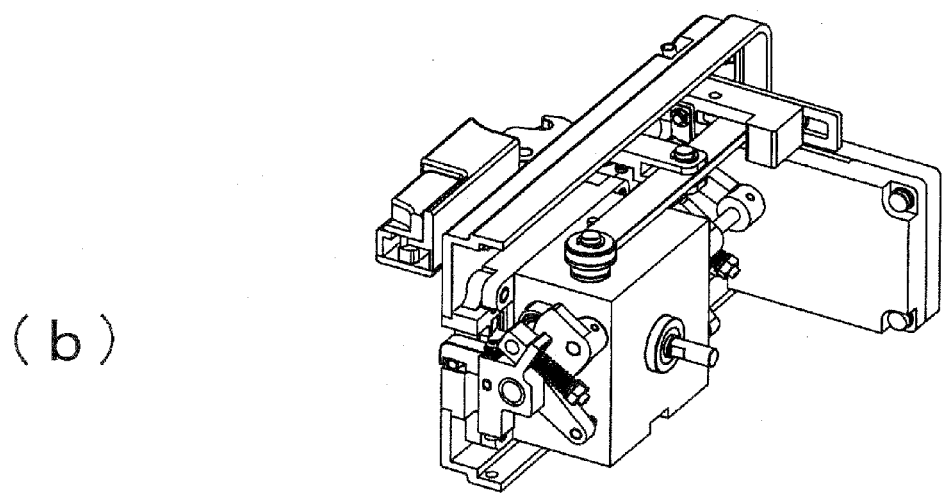

FIG. 5 illustrates a structure of the interlocking mechanism part 13. The interlocking mechanism part 13 is mainly constructed with five links 13A, 13B, 13C, 13D, and 13E.

The five links 13A, 13B, 13C, 13D, and 13E are connected to each other to constitute a link mechanism having a plurality of degrees of freedom and three-axis direction spatial movable range.

A force exerted to a position of one end 13Ai (see FIG. 6) of the link 13A is sequentially transferred to links 13B, 13C, 13D, and 13E.

In the operation of transferring the force, the link 13C exerts a force on the slide part 15A of the slide clamp mechanism part 15, and the link 13E exerts a force on the valve cam shaft 14E of the valve mechanism part 14.

In the state of FIG. 5(a), the slide clamp 30 closing the infusion tube 40 is mounted on the slide clamp mechanism part 15, and the valves 14A and 14B of the valve mechanism part 14 are opened. In this case, any other external forces are not exerted to the position of the end 13Ai of the link 13A of the interlocking mechanism part 13.

If a force is exerted on the end 13Ai of the link 13A through a hook portion 23f of the handle 23, while the handle 23 is moved to a limit position in the movable range of the handle 23, the state of FIG. 5(a) is changed into the state of FIG. 5(b).

In the state of FIG. 5(b), the slide clamp opens the tube due to force exertion of the link 13c of the interlocking mechanism part 13 on the slide clamp mechanism part 15, and the valves 14A and 14B are closed due to force exertion of the link 13E on the valve mechanism part 14.

In the operation of changing the state of FIG. 5(a) into the state of FIG. 5(b), the valves 14A and 14B are closed due to force exertion of the link 13E on the valve cam shaft 14E of the valve mechanism part 14, and after that, the slide clamp 30 opens the infusion tube 40 due to force exertion of the link 13C on the slide part 15A of the slide clamp mechanism part 15.

On the other hand, the state of FIG. 5(b) can be changed into the state of FIG. 5(a) by moving the handle 23 in the reverse direction. In the operation, the slide clamp 30 closes the infusion tube 40 due to force exertion of the link 13C on the slide part 15A of the slide clamp mechanism part 15, and after that, the valves 14A and 14B are opened due to force exertion of the link 13E on the valve cam shaft 14E of the valve mechanism part 14.

FIGS. 6(a) to (d) illustrate positional relationships of the handle 23 with respect to the valves 14A and 14B and the slide clamp 30 operating in interlock with the manipulations of the handle 23 in the corresponding manipulation steps of the handle 23.

For the better understanding of the positional relationships, elements of the door unit 20 except for the handle 23 are omitted in FIGS. 6(a) to (d).

In the state of FIG. 6(a), the handle 23 is located at the position shown in FIG. 6(a) due to weight exertion of the slider spring 15F through the link 13A. In this case, any other external force is not exerted on the handle 23.

The slide clamp 30 is located at the position for closing the infusion tube 40 (see FIG. 3(a)), and the valves 14A and 14B are opened (see FIG. 4(a) and FIG. 5(a)).

In the state of FIG. 6(b), an external force F is exerted on the handle 23. The external force F is exerted on the interlocking mechanism part 13 through a portion of the end 13Ai of the link 13A.

In this case, the slide clamp 30 is located at the position for closing the infusion tube 40 (see FIG. 3(a)), and the valves 14A and 14B are opened (see FIG. 4(a)).

In the state of FIG. 6c, an external force F is further exerted on the handle 23 from the state of FIG. 6(b) In this case, the slide clamp 30 is located at the position for closing the infusion tube 40 (see FIG. 3(a)), and the valves 14A and 14B are closed (see FIG. 4(b)).

In the state of FIG. 6(d), an external force F is further exerted on the handle 23 from the state of FIG. 6c to push the handle 23 to the limit position of the movable range of the handle 23. Therefore, the claw portion 23c of the handle 23 is inserted into the rectangular through-hole 11c of the base plate 11 so that the handle is entirely locked with the pump body 10 (see FIG. 1(b)).

In this case, the slide clamp 30 is located at the position for opening the infusion tube 40 (see FIG. 3(b)), and the valves 14A and 14B are closed (see FIG. 4(b)).

After the handle 23 is unlocked, if the handle 23 is rotated in the reverse direction of manipulations shown in FIGS. 6(a) to (d), the slide clamp 30 and the valves 14A and 14B perform operations of closing or opening the infusion tube 40 in the sequence of the states of FIGS. 6(d), (c), (b), and (a).

According to the above operations, during the opening and closing of the door unit 20 by a series of manipulations of the handle 23, the infusion tube 40 is always closed by one or both of the slide clamp 30 and valves 14A and 14B, so that free flow of a solution in the infusion tube 40 can be entirely prevented.

In addition, in the step where the infusion tube 40 is fitted and the handle 23 is locked with the pump body 10, the valves 14A and 14B are in the state of closing the infusion tube 40. However, in order to perform feed by driving the infusion pump 100, the valves 14A and 14B need to be opened at the suitable time.

As described above, the infusion pump 100 according to the embodiment includes a shuttle-type feeding mechanism. Due to the employment of the shuttle type, the valves 14A and 14B can be opened at the suitable time with a simple structure during the feeding.

Figure 7:
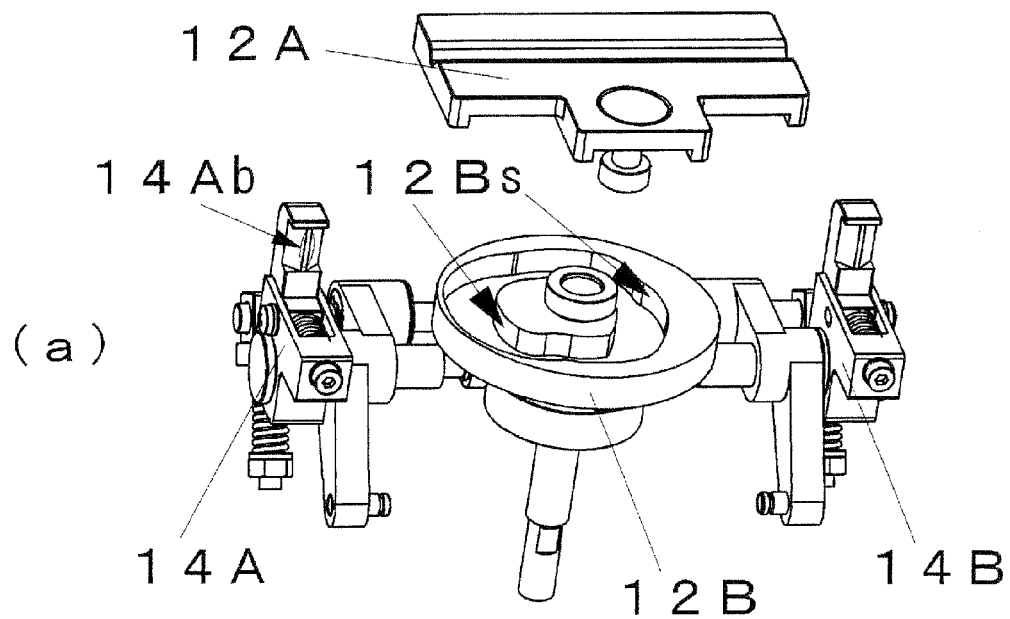
FIGS. 7(*a*), (*b*) and (*c*) are views illustrating a structure of a feeding mechanism according to the embodiment of the present invention.
Figure 7:
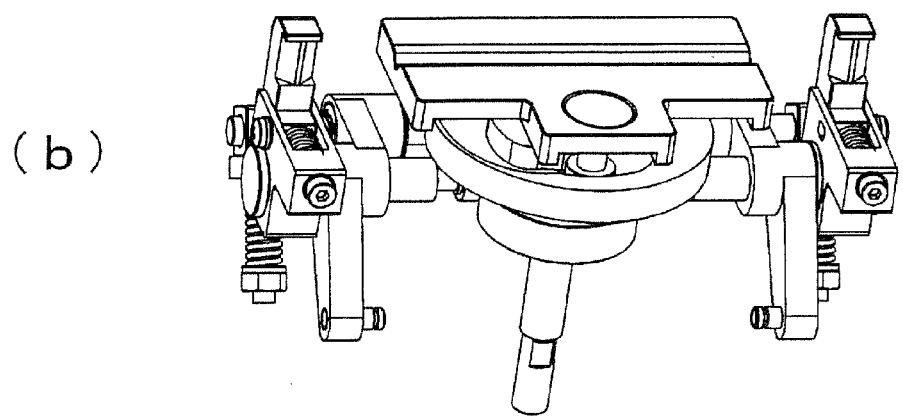
Figure 7:
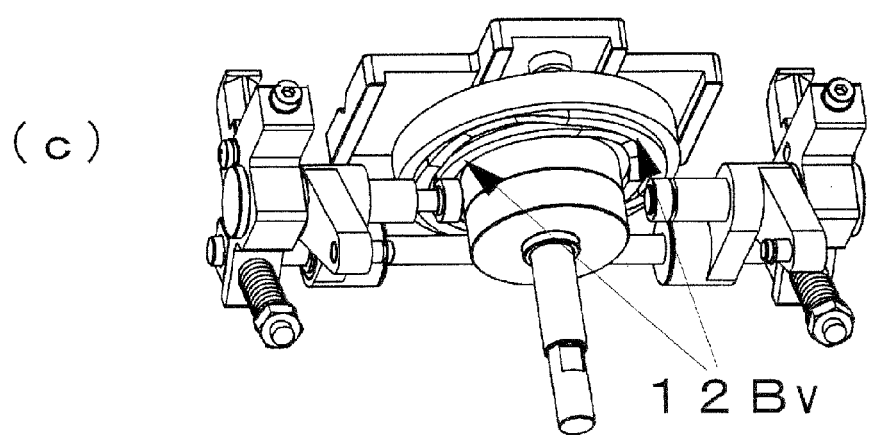

FIG. 7 is a view illustrating a structure of the shuttle mechanism 12 of the infusion pump 100. A pump cam 12B rotating by a driving force of the motor 16 is provided with a cam surface 12Bs for determining a locus of motion of the V-grooved driving part 12A and a cam surface 12Bv exerting a force on the valves 14A and 14B.

The valves 14A and 14B perform closing and opening operations with a respective timing in synchronization with timings of the reciprocating motion of the V-grooved driving part 12A according to the function of the pump cam 12B, so that the feeding can be suitably performed.

When the feeding is not performed, the position of the pump cam 12B is electrically controlled so as for both valves 14A and 14B to be closed. However, even if the pump cam 12B is not stopped at a predetermined position due to some problems of the control, the cam surface 12Bv is formed so that any one of the valves 14A and 14B is always closed.

Due to the above construction of the infusion pump 100 according to the embodiment, free flow can be surely prevented by using a relatively simple construction of parts, and a structure of capable of fitting and unfitting the infusion tube with simple manipulations can be implemented.

FIGS. 8(a) to (d) illustrate side views of an infusion pump 200 according to a second embodiment of the present invention. The infusion pump 200 has a structure where an interlocking mechanism part 13 is provided with a link 13F having a groove cam having a shape shown in FIG. 9.

Similarly to the infusion pump 100 according to the first embodiment, in the infusion pump 200 according to the embodiment, during the opening and closing of a door unit 20 by a series of manipulations of a handle 24, an infusion tube 40 is always closed by one or both of a slide clamp 30 and valves 14A and 14B, so that free flow of a solution in the infusion tube 40 can be entirely prevented.

More specifically, positions of the handle 24 shown in FIGS. 8(a) to (d) correspond to the closing or opening of the infusion tube 40 by the slide clamp 30 and the valves 14A and 14B as the states listed in the following table.

Figure 8:
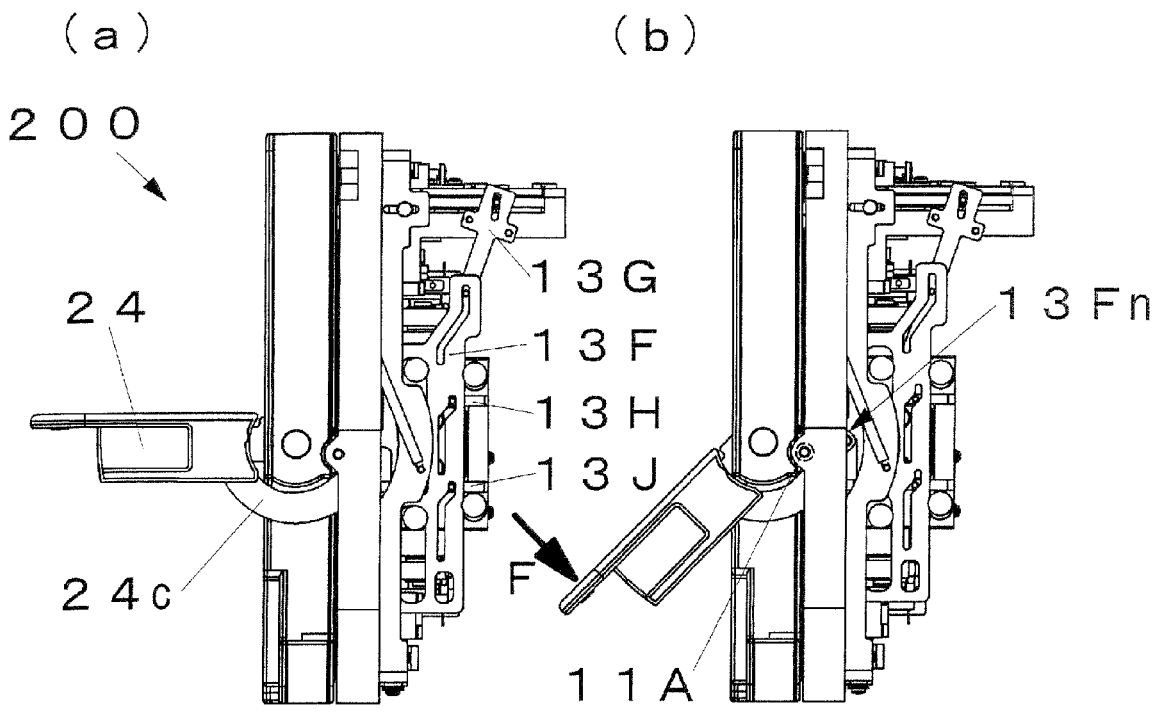
FIGS. 8(*a*), (*b*), (*c*) and (*d*) are views illustrating a positional relationship between a handle and a link according to the embodiment of the present invention.
Figure 8:
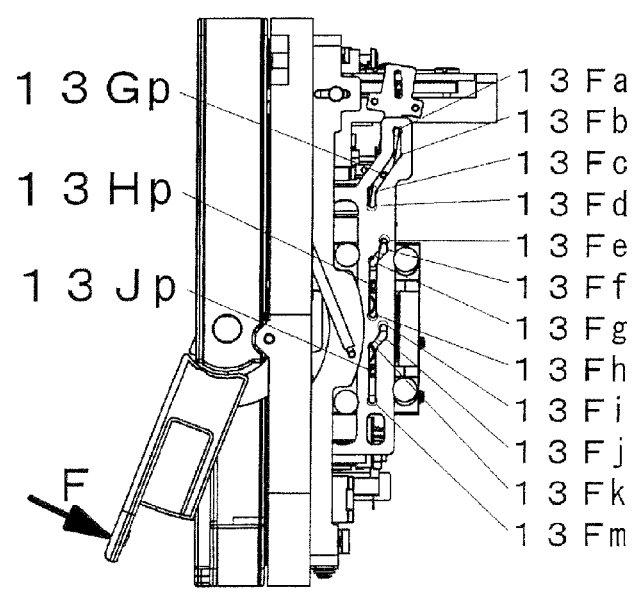
Figure 8:
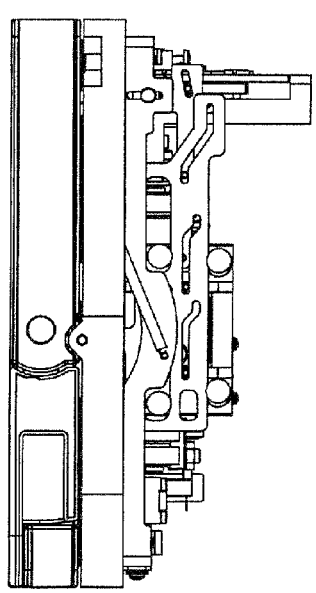
Figure 9:
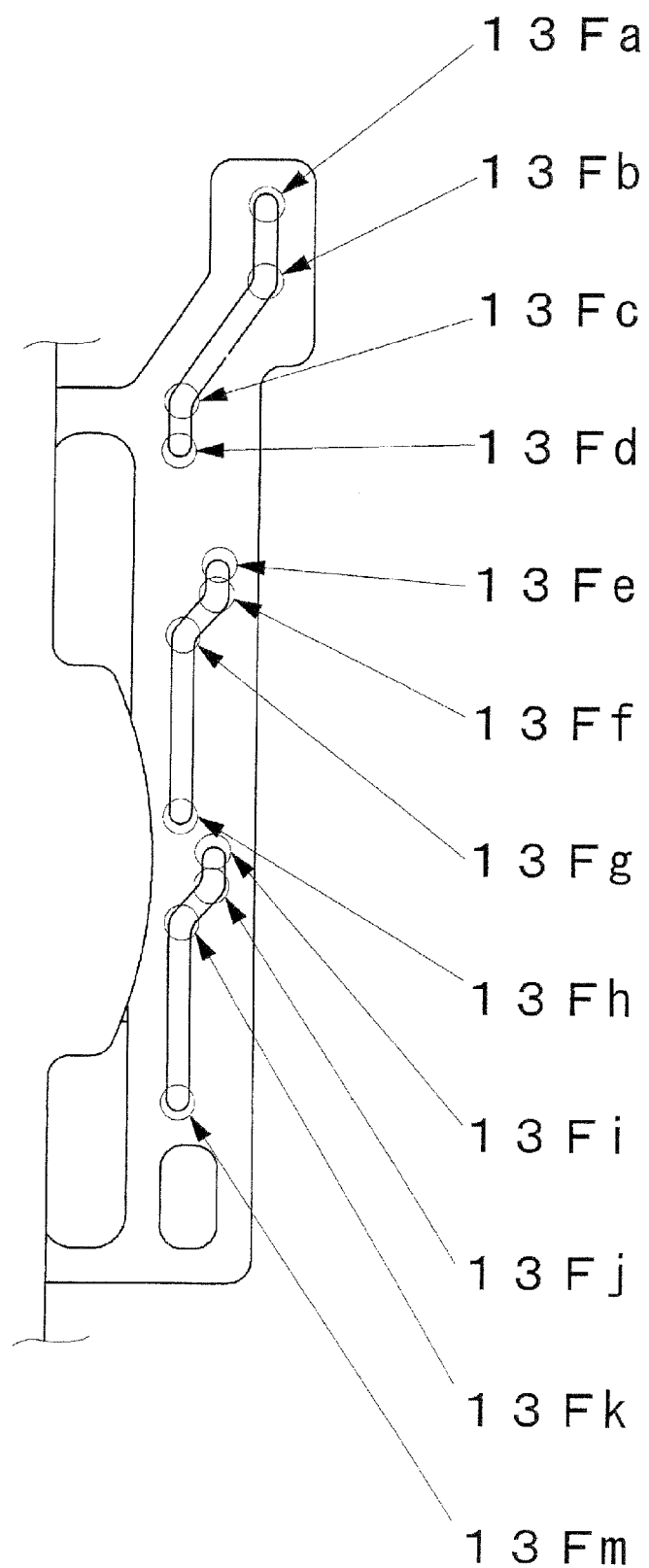
FIG. 9 is a view illustrating a shape of a groove cam according to the embodiment of the present invention.

| Position of Handle (FIG. 8) | Slide Clamp 30 | Valves 14A and 14B |
|---|---|---|
| FIG. 8 (a) | Closed | Opened |
| FIG. 8 (b) | Closed | Opened |
| FIG. 8 (c) | Closed | Closed |
| FIG. 8 (d) | Opened | Closed |

Hereinafter, a structure and function of the infusion pump 200 according to the embodiment for obtaining the states listed in the above table will be described in detail.

A slide clamp mechanism part 15 (see FIG. 3) and a valve mechanism part 14 (see FIG. 4) except for the interlocking mechanism part 13 have the same construction as those of the first embodiment.

In the embodiment, a force is exerted on the link 13F by manipulation of the handle 24, and a link 13G, a link 13H, and a link 13J are operated according to a shape of the groove cam of the link 13F, so that the slide clamp mechanism part 15 and the valve mechanism part 14 are operated in interlock with each other.

More specifically, in the state of FIG. 8(a), the handle 24 is pushed up by force exertion of a spring (not shown) provided to the door unit. In this case, any other external forces are not exerted on the handle 24.

In this case, the slide clamp 30 is located at a position for closing the infusion tube 40 (see FIG. 3(a)), and the valves 14A and 14B are opened (see FIG. 4(a) and FIG. 5(a)).

In the state of FIG. 8(b), an external force F is exerted on the handle 24. The external force F is exerted on the interlocking mechanism part 13 through a portion 13Fn of the link 13F.

In this case, the slide clamp 30 is located at the position for closing the infusion tube 40 (see FIG. 3(a)), and the valves 14A and 14B are opened (see FIG. 4(a)).

In the state of FIG. 8c, an external force F is further exerted on the handle 24 from the state of FIG. 8(b) In this case, a protrusion portion 13Hp of the link 13H is moved from a groove cam portion 13Ff of the link 13F over a groove cam portion 13Fg, and a protrusion portion 13Jp of the link 13J is moved from a groove cam portion 13Fj of the link 13F over a groove cam portion 13Fk, so that the link 13J and the link 13H exert a force on a valve cam shaft 14E.

Due to the force exertion of the link 13J and the link 13H, the valve cam shaft 14E is rotated. Accordingly, the valves 14A and 14B are closed (see FIG. 4(b)), and the slide clamp 30 is located at the position for closing the infusion tube 40 (see FIG. 3(a)).

In the state of FIG. 8(d), an external force F is further exerted on the handle 24 from the state of FIG. 8c to push the handle 24 to the limit position of the movable range of the handle 24. Therefore, a curved arm portion 24c of the handle 24 is stably inserted into the door unit 20 in a state that the curved arm portion is in contact with a latch roller 11A provided to the base plate 11. This state is a state that the handle 24 is entirely locked with the pump body 10.

In addition, in this case, a protrusion portion 13Gp of the link 13G is moved from a portion between a groove cam portion 13Fb and a groove cam portion 13Fc of the link 13F over the groove cam portion 13Fc, so that the link 13G exerts a force on a slide part 15A of the slide clamp mechanism 15. Accordingly, the slide part 15A is moved toward the door unit 20.

In this case, the slide clamp 30 is located at the position for opening the infusion tube 40 (see FIG. 3(b)), and the valves 14A and 14B are closed (see FIG. 4(b)).

If the handle 24 is rotated in the reverse direction of manipulations shown in FIGS. 8(a) to (d), the slide clamp 30 and the valves 14A and 14B perform operations of closing or opening the infusion tube 40 in the sequence of the states of FIGS. 8(d), (c), (b), and (a).

According to the above operations, during the opening and closing of the door unit 20 by a series of manipulations of the handle 24, the infusion tube 40 is always closed by one or both of the slide clamp 30 and valves 14A and 14B, so that free flow of a solution in the infusion tube 40 can be entirely prevented.

An infusion pump according to an embodiment is a peristaltic infusion pump.

A structure of the peristaltic infusion pump is disclosed in Japanese Patent Application Publication No. 5-277183.

Since the peristaltic infusion pump does not need to operate a plurality of valves at the time of feeding a solution, the peristaltic infusion pump is provided with one valve for preventing free flow at the time of fitting of an infusion tube In addition, since the peristaltic infusion pump needs to be in a valve-opened state at the time of operation of feeding the solution, the peristaltic infusion pump is provided with a mechanism for individually opening and closing the valve after fitting the tube in the infusion pump, entirely closing a door unit with respect to a pump body, and closing the valve.

The mechanism for individually opening and closing the valve is operated by a switch using electrical signals generated at the times of starting and stopping the feeding of solution, so that the valve is in the opened state at the time of feeding of solution and in the closed state at the time of stopping the feeding of solution.

Hereinbefore, the first to third embodiments of the infusion pump according to the present invention are described, but various modifications may be implemented without departing from the scope of the present invention.

For example, the interlocking mechanism part is not limited to those of the first and second embodiments, but a mechanism for interlocking the slide clamp mechanism with the valve mechanism only by manipulation of a handle can be constructed with various combinations of links, cams, sliders, springs, and other elements.

In addition, the feeding type is not limited to the shuttle type and the peristaltic type, but any types of infusion pumps that have a door and a handle to feed a solution in an infusion tube in a closed state of the door can be applied.

The invention claimed is:

1. An infusion pump for feeding a solution in an infusion tube,
the infusion pump comprises:
a pump body and a door unit which is openable and closable with respect to the pump body,
wherein the door unit includes a door mechanism part,
wherein the door mechanism part includes a door supported with a first shaft by the pump body and an engagement portion for the pump body and includes a handle which is supported with a second shaft by the door to rotatably move in a predetermined range,
wherein the pump body includes a feeding mechanism part, a slide clamp mechanism part, a valve mechanism part, and an interlocking mechanism part,
wherein the feeding mechanism part has a structure having a driving part for pressing the infusion tube through a reciprocating motion,
wherein the slide clamp mechanism part includes a clamp holding part for holding a clamp member that allows the infusion tube to be in a clamped or unclamped state and a clamp moving part for moving the clamp member,
wherein the valve mechanism part includes a valve capable of blocking a fluid channel of a solution in the infusion tube by pressing on the infusion tube,
wherein the interlocking mechanism part includes a plurality of links sequentially connected to each other and to the door handle to simultaneously control the movement of the slide clamp mechanism part and the valve mechanism part when the door handle is rotated to engage with the interlocking mechanism in the pump body and the door is completely closed,
wherein, when the handle is completely engaged with the interlocking mechanism part and the pump body, the clamp member unclamps the infusion tube, and
when the handle is completely engaged with the interlocking mechanism and the pump body and the door is completely closed, the valve of the valve mechanism part closes the fluid channel of the solution in the infusion tube.

2. The infusion pump according to claim 1,
wherein the driving part of the feeding mechanism part is provided with an approximately V-shaped groove portion along the feeding direction in the infusion tube,
wherein the door part of the door mechanism part is provided with an opposite part where an approximately V-shaped groove portion is formed at an opposite position of the driving part in a state that the door unit is closed, wherein at least one valve of the valve mechanism part is disposed at a position that the infusion tube can be closed at both sides of the driving part, wherein the driving part performs reciprocating motion in a direction perpendicular to the feeding direction and in a direction parallel to the opposite door unit, so that the driving part and the opposite part repetitively press the infusion tube, and wherein the valve is operated in synchronization with a timing that the infusion tube is repetitively pressed, so that the solution in the infusion tube is fed.

3. The infusion pump according to claim 2, wherein the interlocking mechanism part for interlocking and operating the slide clamp mechanism part and the valve mechanism part only through manipulation of the handle has a link mechanism part including the plurality of links and having a plurality of degrees of freedom and a three-axis direction movable range, and wherein springs for forcing the interlocking mechanism part are disposed to at least one or more positions of the pump body.

4. The infusion pump according to claim 2, wherein the interlocking mechanism part for interlocking and operating the slide clamp mechanism part and the valve mechanism part only through manipulation of the handle has a structure where the plurality of links including a link having a groove cam or a slider portion are provided in combination, and wherein springs for forcing the interlocking mechanism part are disposed to at least one or more positions of the pump body.

5. The infusion pump according to claim 1, wherein the driving part of the feeding mechanism part is constructed with a plurality of finger parts, and wherein each of the finger parts performs reciprocating motion, so that distal ends of the finger parts sequentially and repetitively press the infusion tube in the feeding direction to feed the solution in the infusion tube in a peristaltic manner.

6. The infusion pump according to claim 5, wherein the interlocking mechanism part for interlocking and operating the slide clamp mechanism part and the valve mechanism part only through manipulation of the handle has a link mechanism part including the plurality of links and having a plurality of degrees of freedom and a three-axis direction movable range, and wherein springs for forcing the interlocking mechanism part are disposed to at least one or more positions of the pump body.

7. The infusion pump according to claim 5, wherein the interlocking mechanism part for interlocking and operating the slide clamp mechanism part and the valve mechanism part only through manipulation of the handle has a structure where the plurality of links including a link having a groove cam or a slider portion are provided in combination, and wherein springs for forcing the interlocking mechanism part are disposed to at least one or more positions of the pump body.

8. The infusion pump according to claim 1, wherein the interlocking mechanism part for interlocking and operating the slide clamp mechanism part and the valve mechanism part only through manipulation of the handle has a link mechanism part including the plurality of links and having a plurality of degrees of freedom and a three-axis direction movable range, and wherein springs for forcing the interlocking mechanism part are disposed to at least one or more positions of the pump body.

9. The infusion pump according to claim 1, wherein the interlocking mechanism part for interlocking and operating the slide clamp mechanism part and the valve mechanism part only through manipulation of the handle has a structure where the plurality of links including a link having a groove cam or a slider portion are provided in combination, and wherein springs for forcing the interlocking mechanism part are disposed to at least one or more positions of the pump body.

10. The infusion pump according to claim 1, wherein the interlocking mechanism part for interlocking and operating the slide clamp mechanism part and the valve mechanism part only through manipulation of the handle has a link mechanism part including the plurality of links and having a plurality of degrees of freedom and a three-axis direction movable range, and wherein springs for forcing the interlocking mechanism part are disposed to at least one or more positions of the pump body.

11. The infusion pump according to claim 1, wherein the interlocking mechanism part for interlocking and operating the slide clamp mechanism part and the valve mechanism part only through manipulation of the handle has a structure where the plurality of links including a link having a groove cam or a slider portion are provided in combination, and wherein springs for forcing the interlocking mechanism part are disposed to at least one or more positions of the pump body.

* * * * *